(12) United States Patent
Greter

(10) Patent No.: US 9,180,417 B2
(45) Date of Patent: Nov. 10, 2015

(54) COMBINED MIXING AND DISCHARGING DEVICE

(75) Inventor: Andy Greter, Baar (CH)

(73) Assignee: MEDMIX SYSTEMS AG, Rotkreuz (CH)

( * ) Notice: Subject to any disclaimer, the term of this patent is extended or adjusted under 35 U.S.C. 154(b) by 299 days.

(21) Appl. No.: 13/807,897

(22) PCT Filed: Jun. 7, 2011

(86) PCT No.: PCT/CH2011/000135
§ 371 (c)(1),
(2), (4) Date: Dec. 31, 2012

(87) PCT Pub. No.: WO2012/000122
PCT Pub. Date: Jan. 5, 2012

(65) Prior Publication Data
US 2013/0098942 A1   Apr. 25, 2013

(30) Foreign Application Priority Data

Jul. 1, 2010 (CH) ...................................... 1070/10

(51) Int. Cl.
| | |
|---|---|
| *B67D 7/70* | (2010.01) |
| *B01F 13/00* | (2006.01) |
| *A61J 1/20* | (2006.01) |
| *B01F 11/00* | (2006.01) |
| *A61M 5/178* | (2006.01) |
| *A61M 5/315* | (2006.01) |
| *A61M 5/31* | (2006.01) |
| *B01F 15/00* | (2006.01) |

(52) U.S. Cl.
CPC ............... *B01F 13/00* (2013.01); *A61J 1/2096* (2013.01); *B01F 11/0071* (2013.01); *B01F 11/0082* (2013.01); *B01F 13/002* (2013.01);

(Continued)

(58) Field of Classification Search
CPC ............. B01F 11/0082; B01F 11/0071; B01F 13/0023; B01F 13/00; B01F 13/002; A61J 1/2096; A61J 1/2068; A61M 5/1782
USPC ........ 222/136, 387, 386, 386.5, 145.5, 145.6, 222/80, 82, 481, 481.5, 478, 324; 366/130, 366/139, 255, 256, 182.1, 333; 604/82–92
See application file for complete search history.

(56) References Cited

U.S. PATENT DOCUMENTS 3,164,303 A * 1/1965 Trautmann .................... 222/190
3,195,778 A    7/1965 Coates (Continued)

FOREIGN PATENT DOCUMENTS

| CH | 541 481 A | 9/1973 |
|---|---|---|
| EP | 0 974 373 A1 | 1/2000 |

(Continued)

*Primary Examiner* — Lien Ngo
(74) *Attorney, Agent, or Firm* — Sughrue Mion, PLLC

(57) ABSTRACT

A discharging device (1), for mixing and discharging a product, comprising a housing (110) with a reservoir (112). An advancement element (120), displaceable in the housing (110), has a product mixing element (112). A piston (140) displaceable in housing longitudinal direction, serves to eject the product from the reservoir (112) through an outlet opening. The piston (140) has an uncoupled state, in which it can be displaced in the longitudinal direction through the advancement element (120), and a coupled state in which it is coupled to the advancement element (120), and in which it can be displaced in the longitudinal direction relative to the housing (110) by the advancement element (120). In the coupled state, the piston (140) and advancement element (120) airtight seals the reservoir (112) and, in the uncoupled state, the piston (140) and/or the advancement element (120) free/frees at least one proximal venting opening (144) outwardly.

12 Claims, 5 Drawing Sheets

(52) U.S. Cl.
CPC ............ B01F13/0023 (2013.01); *A61J 1/1418* (2015.05); *A61J 1/201* (2015.05); *A61J 1/2055* (2015.05); *A61M 5/1782* (2013.01); *A61M 5/31596* (2013.01); *A61M 2005/3123* (2013.01); *A61M 2005/31508* (2013.01); *B01F 15/00506* (2013.01)

(56) References Cited

U.S. PATENT DOCUMENTS

| | | | | |
|---|---|---|---|---|
| 3,464,412 | A | * | 9/1969 | Schwartz ........................ 604/89 |
| 3,543,967 | A | * | 12/1970 | O'Connor ..................... 222/136 |
| 3,659,749 | A | * | 5/1972 | Schwartz ...................... 222/129 |
| 5,277,342 | A | * | 1/1994 | Dickau et al. ................. 222/387 |
| 5,501,371 | A | * | 3/1996 | Schwartz-Feldman ....... 222/136 |
| 5,957,166 | A | * | 9/1999 | Safabash ......................... 141/26 |
| 6,488,651 | B1 | * | 12/2002 | Morris et al. ................... 604/89 |
| 6,789,750 | B1 | * | 9/2004 | Heldt ............................ 239/490 |
| 7,736,049 | B2 | | 6/2010 | Keller |

FOREIGN PATENT DOCUMENTS

| | | |
|---|---|---|
| WO | 03/084445 A1 | 10/2003 |
| WO | 2007/003063 A1 | 1/2007 |
| WO | 2009/105905 A1 | 9/2009 |

* cited by examiner

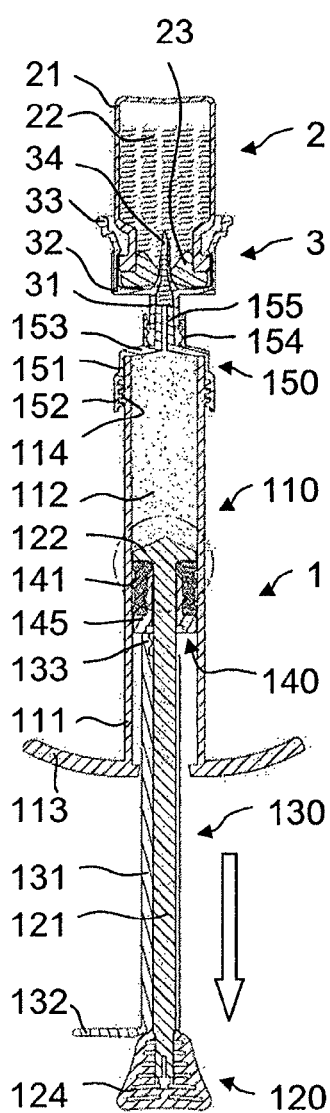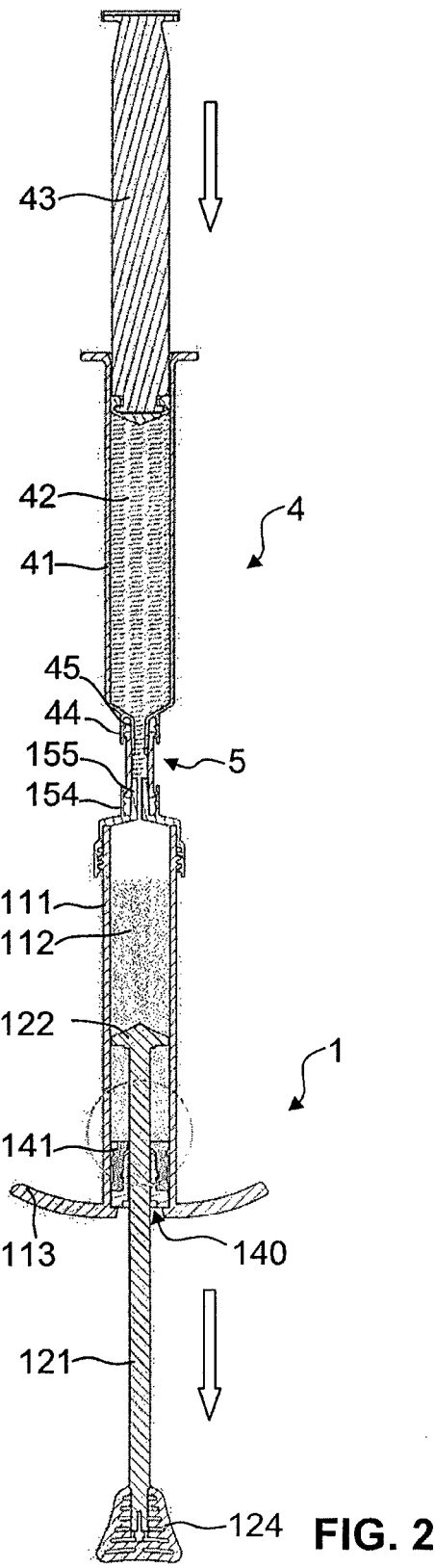
FIG. 1
FIG. 2

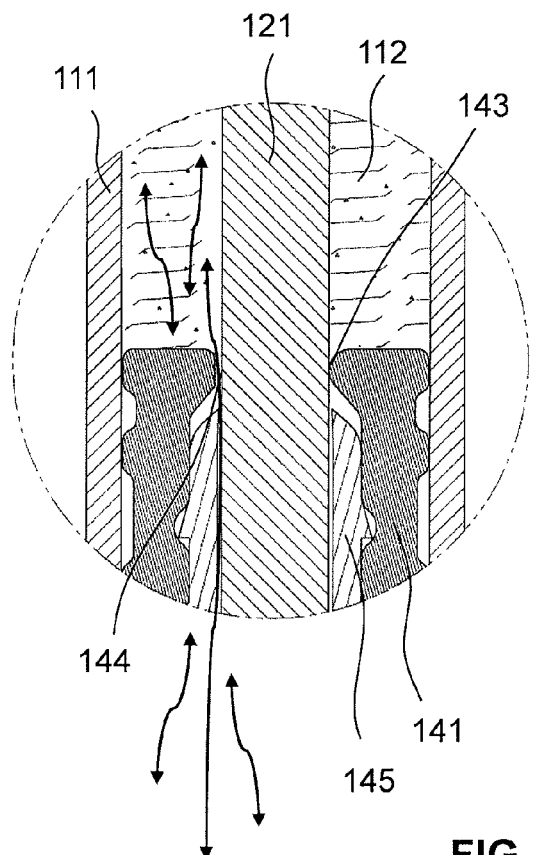
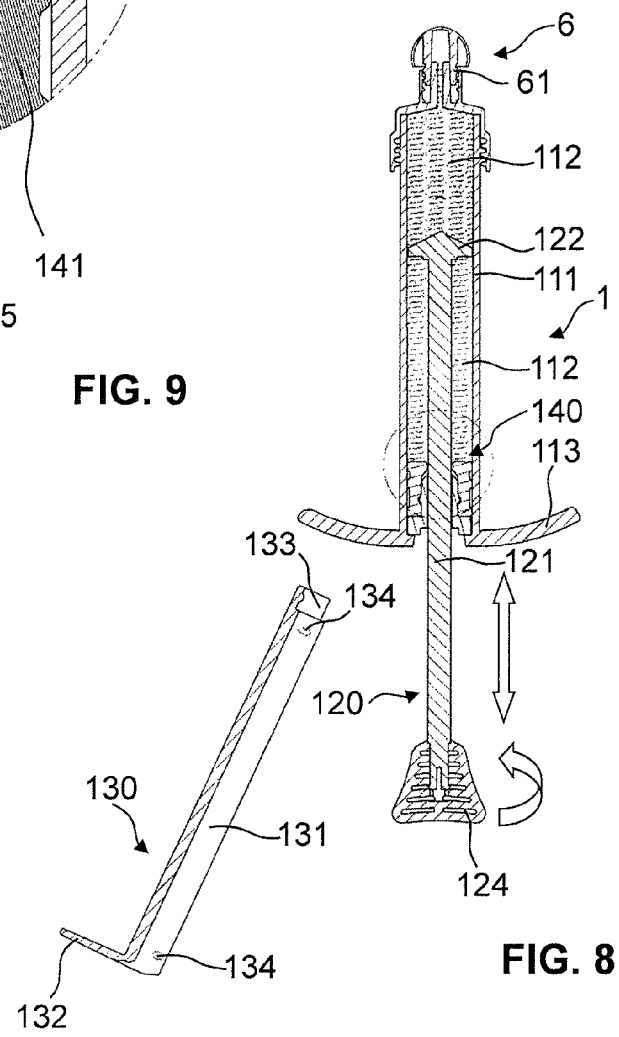
FIG. 9
FIG. 8

COMBINED MIXING AND DISCHARGING DEVICE

CROSS REFERENCE TO RELATED APPLICATIONS

This application is a National Stage of International Application No. PCT/CH2011/000135 filed Jun. 7, 2011, claiming priority bases on Switzerland Patent Application No. 1070/10 filed on Jul. 1, 2010, the contents of all of which are incorporated herein by reference in their entirety.

TECHNICAL FIELD

The present invention relates to a discharging device for mixing and discharging a product. The discharging device comprises a housing, a piston that can be displaced therein, and an advancement element that comprises a mixing element. Such a discharging device can, for example, be used to store a first component, to receive a second component immediately prior to application, to mix said second component with the first component, and to subsequently discharge or apply the mixed product.

PRIOR ART

Discharging devices in the form of syringes have been generally known for a long time. A commercially available syringe comprises a housing with a distal outlet opening and an advancement element that can be slid into the housing from a proximal end. The advancement element comprises a piston rod with a piston affixed distally thereto, which piston is sealingly displaceable in the interior of the syringe body. In order to receive a liquid in the syringe, by means of withdrawing the advancement element in the proximal direction, negative pressure arises in the housing, and consequently the liquid is sucked in through the distal outlet opening. During subsequent displacement of the advancement element in the distal direction the liquid is ejected through the outlet opening.

Some liquid products that are to be applied by means of such a discharging device need to be agitated or mixed immediately prior to application. The liquid product can either be stored already in its full composition in the discharging device, or it is possible for several components of the liquid product to have to be brought together and mixed within the discharging device. In particular, applications are known in which in the discharging device a powdery substance is stored to which immediately prior to the application one or several liquids are to be added and mixed to said powdery substance, e.g. for the preparation of a bone cement as well as in pharmaceutical applications. In order to make possible adequate mixing, in particular also in the case of highly viscous fluids, within the discharging device, discharging devices are known that comprise a mixing device.

Such a discharging device comprising a mixing device is, for example, disclosed in the document U.S. Pat. No. 7,736,049 or in the document WO 2007/003063. Two syringe-like containers are arranged parallel side-by-side and at their outlets are interconnected by way of a valve device. The first, larger, container comprises, for example, a powder, while the second, smaller, container comprises a liquid. In the first container there is a slidable piston through which a mixing rod with a mixing element attached thereto is guided. In the second container there is also a piston, the piston being provided with a piston rod. In order to transfer the liquid from the first container to the second container, the piston of the second container is advanced, by means of the piston rod, in the direction of the outlet so that the liquid accommodated in the second container is pressed into the first container. Subsequently the resulting mixture of powder and liquid is mixed by moving the mixing rod to and fro prior to the mixture being discharged by advancement of the piston of the first container.

When in such a device the liquid is pressed into the first container, it displaces and compresses the air that is present in the first container. Consequently, a dangerous overpressure can arise in the first container. For this reason it is desirable to design the first container in such a manner that, if necessary, air can escape in the region of the piston.

However, if the first container is designed in such a manner that the region of the piston is permeable to air, it is not possible to suck the liquid into the first container by withdrawing the piston of the first container, because it is not possible to generate a vacuum in the first container. It is thus not possible with the use of one and the same device to optionally place the liquid into the second container by sliding in the piston of the second container or by withdrawing the first piston; instead, because of the design of the discharging device the user is restricted to one of these two options. Furthermore, it is disadvantageous if air can enter through the region of the piston into the first container, because it is possible that as a result of this the chemical characteristics of the product received in the first container are altered during storage.

A further discharging device with a mixing device is disclosed in the document WO 2009/105905. The discharging device comprises a container with a piston slidable therein, through which a mixing rod is fed. At the distal end of the mixing rod a mixing element is arranged. The mixing rod is displaceable relative to the piston, but it can be affixed to the piston by means of a securing element. Thus, when the mixing rod has been affixed to the piston, the substances to be applied can be drawn into the container and can be ejected from said container. In the non-affixed state, during mixing of the substances, the piston remains immovable relative to the container, while the mixing rod with the mixing element is moved forwards and backwards in longitudinal direction.

While in such a design it is possible, without further ado, to suck up a liquid into the container by retracting the piston, in those cases where the user would like to fill liquid into the container by injecting the liquid into said container by means of a separate syringe, again, dangerous overpressure can result in the container. Moreover, when the substances received in the housing are mixed by means of the mixing device, in such a device negative pressure or positive pressure can result. During subsequent opening of the outlet opening, any remaining positive pressure or negative pressure in the container can result in part of the product being ejected from the container or in air being sucked in. This is problematic, in particular in the case of toxic products, highly corrosive products or in products requiring precise dosing.

SUMMARY OF THE INVENTION

It is a first object of the present invention to provide a discharging device with a mixing device that makes it possible to draw in a liquid optionally with the application of negative pressure or to transfer it to the discharging device by injection from the outside without this resulting in dangerous overpressure. As an alternative it is a second object of the present invention to provide a discharging device with a mixing device that makes it possible by injection from the outside to transfer a liquid into the discharging device without this resulting in dangerous overpressure, which discharging device nevertheless ensures that during storage no air can get into the discharging device. It is an alternative third object of the present invention to provide a discharging device with a mixing device that makes it possible to draw in a liquid by the application of negative pressure, in which discharging device, however, any positive pressure or negative pressure during the mixing process is avoided.

The present invention provides a discharging device for mixing and discharging a product, comprising:

a housing that delimits a reservoir for the product, with a circumferential sidewall, an open proximal housing end and a distal housing end with an outlet opening;

an advancement element that projects into the housing from the direction of the proximal housing end and that can be slid along a longitudinal direction relative to the housing, wherein the advancement element comprises a distal region with a mixing element for mixing the product; and a piston that is proximally arranged relative to the mixing element and that can be slid relative to the housing in the longitudinal direction in order to eject the product from the reservoir through the outlet opening.

The piston comprises an uncoupled state in which the advancement element can be displaced in the longitudinal direction relative to the piston, and comprises a state in which it is coupled to the advancement element, in which state the piston can be displaced in the longitudinal direction relative to the housing by means of the advancement element.

In the coupled state the piston, together with the advancement element, seals the reservoir in an airtight manner in the proximal direction towards the outside. In the uncoupled state the piston and/or the advancement element free/frees at least one proximal venting opening in the outward direction.

As a result of the piston being retracted in the coupled state by means of the advancement element it becomes possible to suck a liquid into the reservoir. When, on the other hand, a liquid is to be injected into the discharging device by means of a syringe, the piston can be moved to the uncoupled state. Air present in the housing can then escape towards the outside through the venting opening, and consequently any build-up of positive pressure is prevented.

Furthermore, in the uncoupled state any positive pressure or negative pressure that may arise during mixing of two or more components received in the reservoir can be equalised towards the outside. Such positive pressure or negative pressure can, in particular, arise when during mixing of the components the advancement element, which can comprise a piston rod with a mixing element attached thereto, is displaced forwards or backwards relative to the housing. During advancement of the advancement element into the housing, the aforesaid projects further and further into the reservoir and, because of its displacement volume, requires more and more space, as a result of which positive pressure can arise in the reservoir. During withdrawal of the advancement element relative to the housing, correspondingly, negative pressure can arise. However, positive pressure or negative pressure can also arise as a result of chemical reactions during mixing, e.g. polymerisation reactions with the release of a gas. By comprising at least one venting opening, the discharging device can equalise this positive pressure or negative pressure towards the outside.

In the coupled state the reservoir is nevertheless closed off in an airtight manner in the proximal direction for storage, drawing up and ejecting the product.

In the following, directions are indicated as follows. The longitudinal direction denotes the direction of displacement of the advancement element. The distal direction is the direction in which the piston is advanced towards an outlet opening for the purpose of discharging a product received in the discharging device. The proximal direction denotes the direction opposite the aforesaid.

The product received in the reservoir can, for example, be several components of a medicament to be mixed or several components of a medical or non-medical adhesive or of a bone cement. It is then advantageous if only one of these components is received in the discharging device in the storage state. Further components can then be transferred to the reservoir, for example immediately prior to applying or administering the product, for example from a vial or a commercially available syringe.

In the coupled state of the piston the discharging device can be used like a commercially available syringe; in other words a liquid product can be drawn into the reservoir and can be ejected from said reservoir by means of the advancement element. Since the reservoir is then sealed off so as to be airtight in the proximal direction, negative pressure results in the reservoir when the advancement element is withdrawn from the housing, and positive pressure results in the reservoir when the advancement element is advanced into the housing, wherein the positive pressure or negative pressure is then desired in order to eject or draw in the product. Preferably, in this arrangement in the coupled state the piston is connected to the advancement element in such a manner that it is immovable in longitudinal direction relative to the advancement element.

Preferably, the advancement element extends through the piston. In the coupled state the piston then rests in an airtight manner both against the advancement element and against the housing so as to completely seal off the reservoir in the proximal direction. In the uncoupled state it is then possible, for example, for an air passage between the piston and the advancement element and/or between the piston and the housing to be present.

Preferably, the at least one venting opening is arranged on the piston, wherein in the coupled state the advancement element closes off the venting opening in an airtight manner. In a preferred embodiment the at least one venting opening is closed off by the mixing element in the closed state. The mixing element can then in a region situated opposite the venting opening comprise a correspondingly designed closing element.

Advantageously the at least one venting opening is designed as a radial indentation. This means that the venting opening is then not fully enclosed by the material of the piston. In this arrangement the radial indentation can, in particular, be formed on a radial outside or inside of the piston.

However, the venting opening is preferably arranged on a radial inside of the piston. Advantageously the radial inside of the piston then comprises a radially circumferential contact region in the region of the venting opening, which contact region widens in the distal direction radially towards the outside. The contact region can have a surface normal that is inclined relative to the longitudinal direction, in particular at an angle of approximately 45°. If the piston comprises such a contact region, advantageously the advancement element comprises a radially circumferential recess with an outside edge, which outside edge in the coupled state rests against the contact region so as to provide a circumferential, airtight seal.

Advantageously the piston and the advancement element seal the reservoir both in the coupled state and in the uncoupled state in such a manner that the reservoir in the proximal direction is impermeable towards the outside for powdery and paste-like substances. Any leakage of the product stored in the reservoir in the uncoupled state, and in particular during the mixing process, is thus prevented.

Preferably, the piston comprises a carrier sleeve and a sealing element, affixed to the carrier sleeve, which sealing element encloses the carrier sleeve. The carrier sleeve is used for holding the sealing element. The sealing element advantageously comprises a flexible and elastic material, while in contrast to this the holding element is designed so as to be rigid. In this arrangement the venting opening is advantageously arranged on the sealing element.

In the uncoupled state any displacement of the piston relative to the housing in the proximal direction can result in air being sucked into the reservoir from the outside. This is advantageously prevented in that the piston can be decoupled from the advancement element only if the piston has been retracted from the housing up to a proximal end stop. To this effect the discharging device can, for example, comprise a securing element by means of which the piston can be coupled to the advancement element. The securing element can, for example, be designed in such a manner that it only allows decoupling if the piston has been withdrawn from the housing up to a proximal end stop.

Preferably, the securing element can be attached to the advancement element so that it is non-displaceable in the longitudinal direction so that the piston is fixed in the longitudinal direction between the securing element and the advancement element, thus being coupled to the advancement element. In this arrangement the securing element can, in particular, be removable from the advancement element in order to decouple the piston from the advancement element. However, preferably the securing element is removable from the advancement element only if the piston has been withdrawn from the housing up to a proximal end stop. This can, in particular, be implemented for example in that the securing element has an elongated shape and can be slid into the reservoir together with the advancement element. Because of the radial delimitation by the housing, removal of the securing element from the advancement element is then advantageously possible only when the securing element together with the advancement element has largely been withdrawn from the housing. The securing element can also, as described for example in WO 2009/105905, be pivotally connected to a proximal region of the advancement element. Pivoting the securing element relative to the advancement element, in order to couple or decouple the piston to/from the advancement element, is then only possible when the securing element has been withdrawn from the housing and when the advancement element and the piston form a proximal end stop with the housing.

Advantageously, in the coupled state the piston forms a distal end stop at the mixing element.

In the coupled state the securing element in the proximal direction preferably forms an end stop with an element of the advancement element that is arranged in the region of the proximal end of the advancement element. In this arrangement the securing element in the coupled state advantageously forms an end stop, in the proximal direction, with an actuating handle affixed to the advancement element, while in the distal direction forming an end stop with the piston.

BRIEF DESCRIPTION OF THE DRAWINGS

Below, preferred embodiments of the invention are described with reference to the drawings, which are only provided for clarification and are not to be interpreted as being limiting. The following is shown in the drawings:

FIG. 1 a central section view of a discharging device according to the invention according to a first embodiment, with a vial connected thereto, during drawing-in of a liquid;

FIG. 2 a central section view of the discharging device of FIG. 1 with a syringe connected thereto, during drawing-in of a liquid;

FIG. 8 a central section view of the discharging device of FIG. 1, with an end cap connected thereto, during mixing of the product;

FIG. 9 a partial section view of the region marked in FIG. 8;

DESCRIPTION OF PREFERRED EMBODIMENTS

Figure 3:
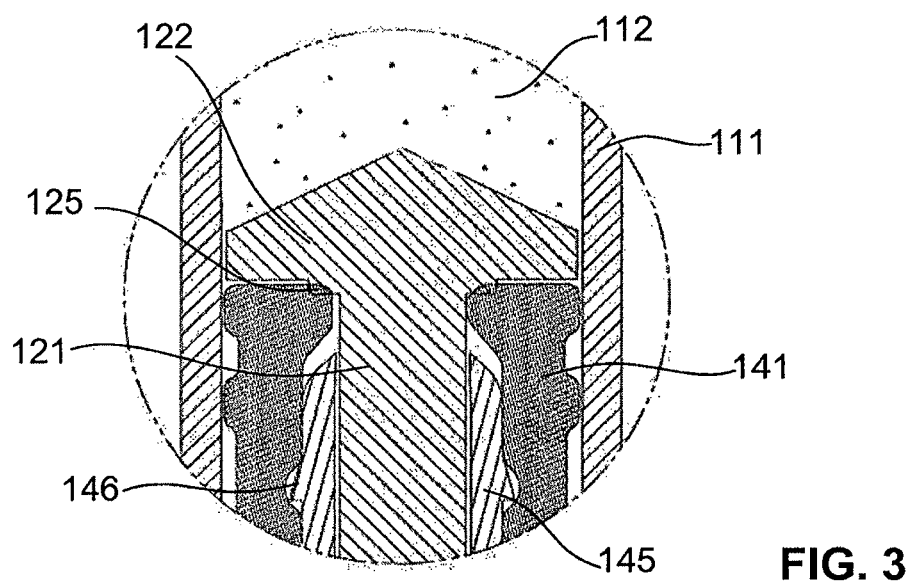
FIG. 3 a partial section view of the region marked in FIGS. 1 and 2.

FIGS. 1 to 11 show a discharging device 1 according to the invention according to a preferred embodiment. The discharging device 1 of this embodiment is a syringe which is used, for example, for mixing and administering a medicament or for mixing and discharging an adhesive or a bone cement. The discharging device 1 comprises a housing 110 in which an advancement element 120 is slidably arranged along an axial longitudinal direction. In this arrangement the advancement element 120 is slid from a proximal end into the housing 110. In the housing 110, furthermore, a piston 140 is arranged that is slidable in the longitudinal direction relative to the housing 110 and to the advancement element 120. In the present embodiment, in addition, a securing element 130 can be affixed to the advancement element 120, and at the distal end a connection attachment 150 is screwed onto the housing 110.

The housing 110, which can also be referred to as a syringe body, comprises a circumferential sidewall 111 that forms a hollow cylinder, which sidewall 111 has a proximal end and a distal end. The sidewall 111 delimits a cylindrical reservoir 112 that extends in its interior. By its cylindrical form the reservoir 112 thus defines an axial longitudinal direction, and a direction that is radial to the aforesaid, of the discharging device 1 as well as a reservoir centre axis. In the region of the proximal end of the sidewall 111 at diametrically opposed sides two radially-outward-protruding holding wings 113 are arranged. In this arrangement the holding wings 113 are slightly curved towards the distal direction. From the proximal housing end the reservoir 112 is accessible through a proximal opening in the housing 110, wherein the proximal housing opening comprises an internal diameter that is smaller when compared to that of the sidewall 111. In the region of the distal housing end the sidewall 111 comprises a circumferential external thread 114.

The connection attachment 150 comprises a covering surface 153 with a circumferential jacket 151. On the inside of the jacket 151 there is an internal thread 152 that is designed so as to be complementary to the external thread 114 of the housing 110. On the side opposite the jacket 151 the covering surface 153 comprises a male Luer cone 155 that encloses a distal outlet opening of the housing 110, and a locking sleeve 154 that is concentric to the aforesaid. The locking sleeve 154, which comprises an internal thread, together with the male Luer cone 155 forms a connection of the discharging device 1, which connection is suitable for connecting various connection elements, for example vials 2, other syringes, injection needles 7 or connection adapters 5.

The advancement element 120 comprises a piston rod 121 that is elongated in the longitudinal direction, with a mixing element 122 being formed at its distal end. The mixing element 122 extends from the piston rod 121 in the radial direction. In this arrangement the mixing element 122 can be designed in various ways according to the state of the art. For example, said mixing element 122 can comprise an outer ring that is arranged so as to be concentric to the piston rod 121, which ring is connected to the piston rod 121 by way of several straight or curved webs. However, the mixing element 122 can also be designed as a plate that comprises several through-openings. Advantageously the mixing element 122 has an external diameter that is only slightly smaller than the internal diameter of the sidewall 111 of the housing 110. On the proximal side of the mixing element 122 in the transition region between the mixing element 122 and the piston rod 121 a circumferential recess 125 is formed which from the piston rod 121 extends only slightly radially outwards, which recess 125 comprises an outside edge. At the proximal end of the piston rod 121, an actuating handle 124 is affixed by means of a snap-on connection.

The securing element 130, which is shown in particular in FIG. 8, in the present exemplary embodiment comprises a main section 131 that comprises a curved cross section. In this arrangement the cross section of the main section 131 extends over an angular range around the longitudinal axis, which angular range slightly exceeds 180°. On its radial inside the main section 131 can comprise detent lugs 134. At its distal end the main section 131 makes a transition to an end stop element 133. At the proximal end of the main section 131 a gripping wing 132 is attached that protrudes radially outwards at a right angle.

Figures 4, 5:
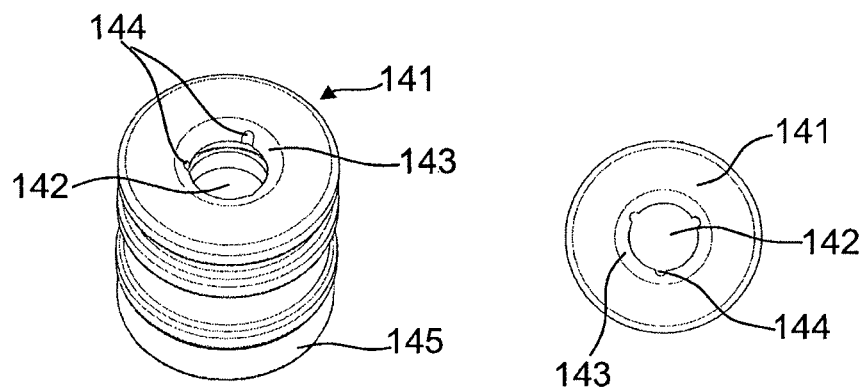
FIG. 4 a perspective view of the piston of the discharging device shown in FIG. 1.
FIG. 5 a lateral view of the piston of the discharging device shown in FIG. 1.

The piston 140 of the present embodiment is shown in particular in FIGS. 4 and 5. In the present embodiment the piston 140 comprises a sealing element 141 and a carrier sleeve 145. The sealing element 141 has an essentially hollow-cylindrical shape with a through opening. At the radial outside of the sealing element 141 there are several circumferential elevations which delimit indentations that are arranged between them. On the radial inside of the sealing element 141 there is a circumferential detent groove. In addition, in the region of the distal end of the sealing element 141 there is a circumferential sealing lip that projects radially inwards, and consequently the through-opening of the sealing element 141 is constricted at this position. In the distal direction this sealing lip radially widens towards the outside, thus forming a contact region 143. The sealing lip comprises several, in the present embodiment precisely three, radial indentations 144 that form venting openings of the piston 140. In this arrangement the indentations 144 are regularly spaced apart from each other circumferentially and are designed so as to be open radially inwards.

The carrier sleeve 145 forms a holding element that is used to hold the sealing element. The carrier sleeve 145 comprises a connection region that extends in the longitudinal direction and that is designed so as to be essentially hollow-cylindrical in shape and comprises an axial through-opening 142. On the radial outside of this connection region there are several detent elements 146. On the proximal end of the connection region there is a circumferential flange that radially projects towards the outside. In an alternative embodiment the carrier sleeve 145 could, however, also be omitted. The piston 140 could then for example comprise only a sealing element.

In the present embodiment the housing 110, the advancement element 120 (except for the actuating handle 124), the securing element 130, the carrier sleeve 145, the sealing element 141 and the connection attachment 150 are each made in one piece from plastic in an injection moulding process. In this arrangement the sealing element 141 is made from a particularly elastic and flexible plastic. However, in another embodiment the piston 140 could also be made in one piece and could, for example, be made in a two-component injection moulding process. Also, the connection attachment 150 could be connected to the housing 110 directly in one piece. Likewise, the actuating handle 124 could be affixed in a single piece to the piston rod 121.

The interaction of the different elements and the function of the discharging device 1 is described below with reference to FIGS. 1 to 11.

In the reservoir 112 of the discharging device 1 shown in FIG. 1 a powdery first substance is stored. In the situation shown in FIG. 1 a liquid is drawn up from a vial 2 into the discharging device 1. In this arrangement, in the proximal direction the reservoir 112 is closed off by the advancement element 120 and the piston 140, which are interconnected. The advancement element 120 projects through the piston 140 and with the proximal side of the mixing element 122 rests against said mixing element 122. The sealing element 141 has been placed onto the carrier sleeve 145 so that the aforesaid projects from the proximal side of the sealing element 141 into said sealing element 141. In this arrangement the detent elements 146 of the carrier sleeve 145 have snapped into the detent groove formed on the radial inside of the sealing element 141. On its radial outside the sealing element 141 rests circumferentially and in an airtight manner against the sidewall 111. The recess 125 of the mixing element 122, furthermore, rests circumferentially and in an airtight manner against the contact region 143 of the piston 140. Furthermore, said recess 125 also closes off the radial indentations 144 of the piston 140. Consequently the reservoir 112 is closed off in an airtight manner in the proximal direction.

The securing element 130 is affixed to the piston rod 121 in such a manner that it encloses the aforesaid with its U-shaped cross section. In this arrangement the securing element 130 is clamped between the actuating handle 124 and the radially protruding flange of the carrier sleeve 145, and consequently the securing element 130 pushes the piston 140 against the mixing element 122 and in particular against the recess 125, thus sealing the passage between the contact region 143 and the recess 125 in an airtight manner. The piston 140 is thus coupled to the advancement element 120 and by means of the aforesaid can be displaced relative to the housing 110 in the longitudinal direction. Thus the mixing element 122 then forms a distal end stop for the piston 140. In this arrangement the sealing element 141 is slightly compressed in the longitudinal direction and consequently is pushed in the radial direction outwards towards the sidewall 111 as well as inwards towards the piston rod 121. At the proximal end of the housing 110 the securing element 130 with the main section 131 rests against the inside edge of the proximal housing opening, and consequently any dislodging of the securing element 130 from the piston rod 121 in this position is impossible.

A connection element 3 is connected to the Luer connection 154, 155 of the connection attachment 150 screwed onto the housing 110, in which connection element 3 a vial 2 is held. To this extent the connection element 3 comprises a female Luer cone 31 with an external thread and a receiving region 32 for receiving the vial 2. A piercing element 34 of the connection element 3 is used to pierce open a closing element 23 of the vial 2 and to establish a connection to a reservoir 22 that is delimited by a container wall 21 of the vial 2. Release handles 33 affixed to the connection element 3 facilitate separation of the vial 2 from the connection element 3.

In the present example the reservoir 22 of the vial 2 comprises a liquid that is drawn into the reservoir 112 of the housing 110 in that the advancement element 120 with the piston 140 is pulled in the proximal direction (direction of arrow in FIG. 1) from the housing 110. Because the piston 140 rests in an airtight manner against the sidewall 111 on the one hand and against the advancement element 120 on the other hand, this results in negative pressure in the reservoir 112, and consequently the liquid stored in the reservoir 22 of the vial 2 is drawn into the reservoir 112 through the outlet opening enclosed by the Luer cone 155.

Instead of from a vial 2 the liquid can also be transferred to the reservoir 112 from a syringe 4, as shown in FIG. 2. To this effect the Luer connection 154, 155 of the discharging device 1 can be connected by way of a connection adapter 5 to a male Luer cone 45 designed in the same manner and to a locking sleeve 44 of the syringe 4. Such a commercially available syringe 4 comprises a housing 41 with a reservoir 42 into which a piston unit 43 can be slid in order to eject a fluid product from the reservoir 42 in a known manner. Transferring the liquid contained in the syringe 4 to the reservoir 112 of the discharging device 1 can in principle take place in the same manner as described above in the context of transfer from a vial, i.e. in that the advancement element 120 with the securing element 130 affixed thereto is withdrawn, wherein the piston 140 closes off the reservoir 112 in an airtight manner and generates negative pressure. In the example of FIG. 2, however, the transfer takes place in a different manner. In this example the discharging device 1 was delivered in a state in which the piston 140 is from the very beginning in a proximal end position within the housing 110. In this position the securing element 130 was removed, and the advancement element was advanced through the piston 140 to such an extent in the distal direction that the mixing element 122 no longer rests against the sealing element 141. Consequently, the radial indentations 144, which act as venting openings, on the sealing element 141 are unblocked, as will be explained in more detail below in the context of FIG. 9. The liquid is then transferred from the syringe 4 to the reservoir 112 in that the piston unit 43 of the syringe is pushed into the syringe. In this process the liquid reaching the reservoir 112 displaces the air that was initially present therein and is absorbed by the powdery substance. However, the air can escape through the venting openings. This makes it possible to fill the reservoir 112 without any positive pressure arising.

Figures 6, 7:
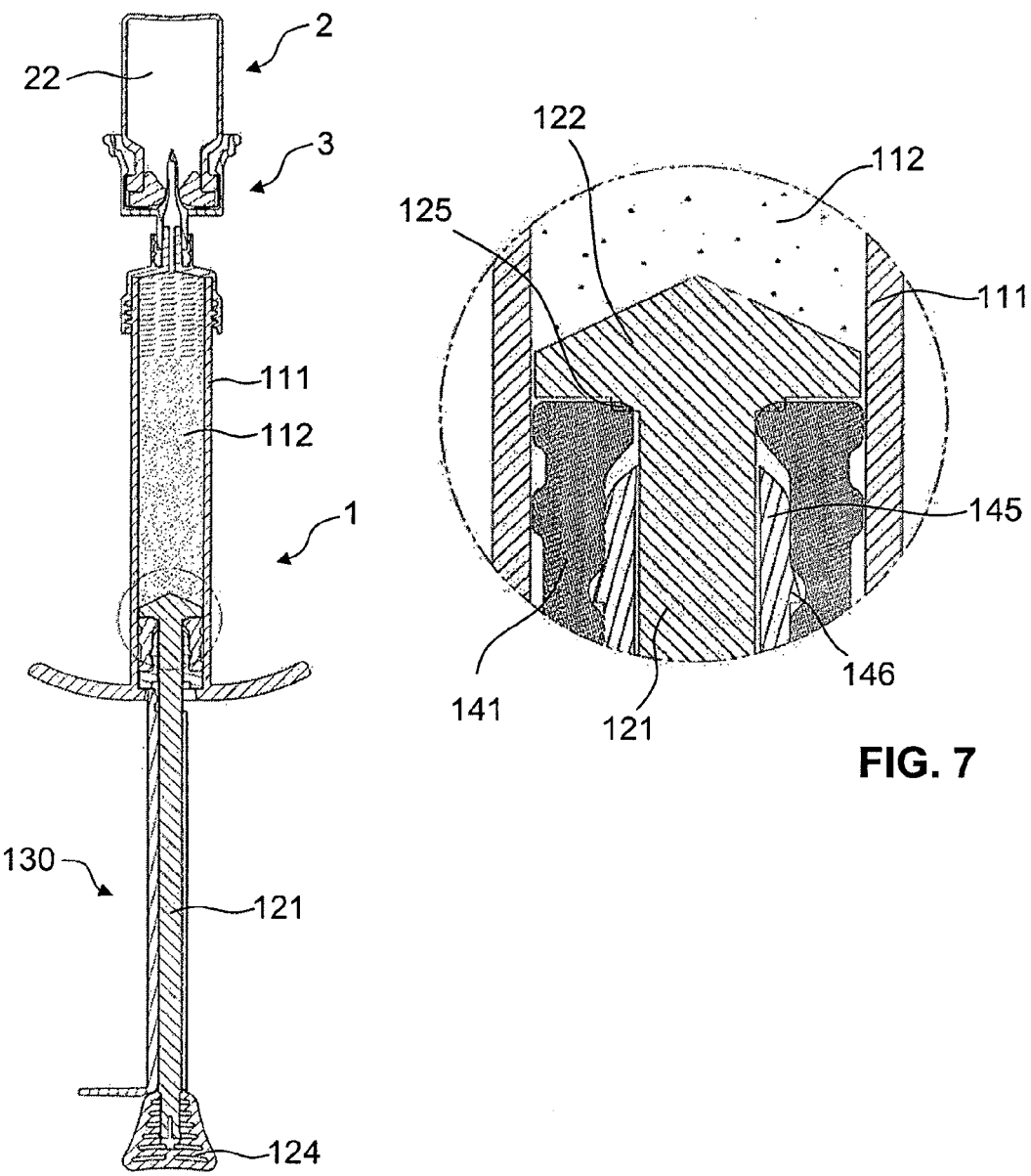
FIG. 6 a central section view of the discharging device of FIG. 1, with a vial connected thereto, after completion of drawing-in a liquid.
FIG. 7 a partial section view of the region marked in FIG. 6.

FIGS. 6 and 7 show a situation in which a liquid was fully transferred from the vial 2 to the reservoir 112 of the discharging device 1. In this arrangement the advancement element 120 is pulled from the housing 110 to such an extent that the carrier sleeve 145 of the piston 140 forms a proximal end stop in the region of the proximal end of the housing 110. However, the drawn-in liquid and the powdery substance are not yet completely intermixed; instead they still form two phases. In the position of the advancement element 120 relative to the housing 110, as shown in FIG. 6, the securing element 130 can be removed from the piston rod 121.

After removal of the securing element 130 from the advancement element 120 (FIGS. 8 and 9), the piston 140 is in an uncoupled state relative to the advancement element 120. The advancement element 120 is then slidable in the longitudinal direction relative to the piston 140. Since overall a larger surface of the sealing element 141 rests against the sidewall 111 than against the piston rod 121, during displacement of the advancement element 120 the piston 140 remains immovable relative to the housing 110 because of the resulting frictional forces. Thus for the purpose of mixing the liquid with the powdery substance in the reservoir 112, the advancement element 120 can be moved at will to and fro and around the longitudinal axis (directions of arrows in FIG. 8) without in this process moving the piston 140 from its position in the proximal region of the housing 110. By means of the mixing element 122 the two substances can be mixed with each other. In this arrangement the distal outlet opening of the discharging device 1 is advantageously closed off by an end cap 6 in order to prevent any discharge of the substances to be mixed. To this effect the end cap 6 comprises a female Luer cone 61 with an external thread.

Because the mixing element 122, and in particular the recess 125, in the uncoupled state no longer rest against the sealing element 141, an air-permeable passage from the reservoir 112 through the radial indentations 144 and through the remaining space between the piston rod 121 and the through-opening 142 of the carrier sleeve 145 is opened up towards the outside (see arrows in FIG. 9). Negative pressure or positive pressure arising in the reservoir 112 due to the movements of the mixing element 122 as a result of its displacement volume or as a result of chemical reactions is thus equalized towards the outside. However, because of the small dimensions of the radial indentations 144 the reservoir 112 continues to be impermeable, even in this uncoupled state, towards the outside to powdery and paste-like substances.

Figures 10, 11:
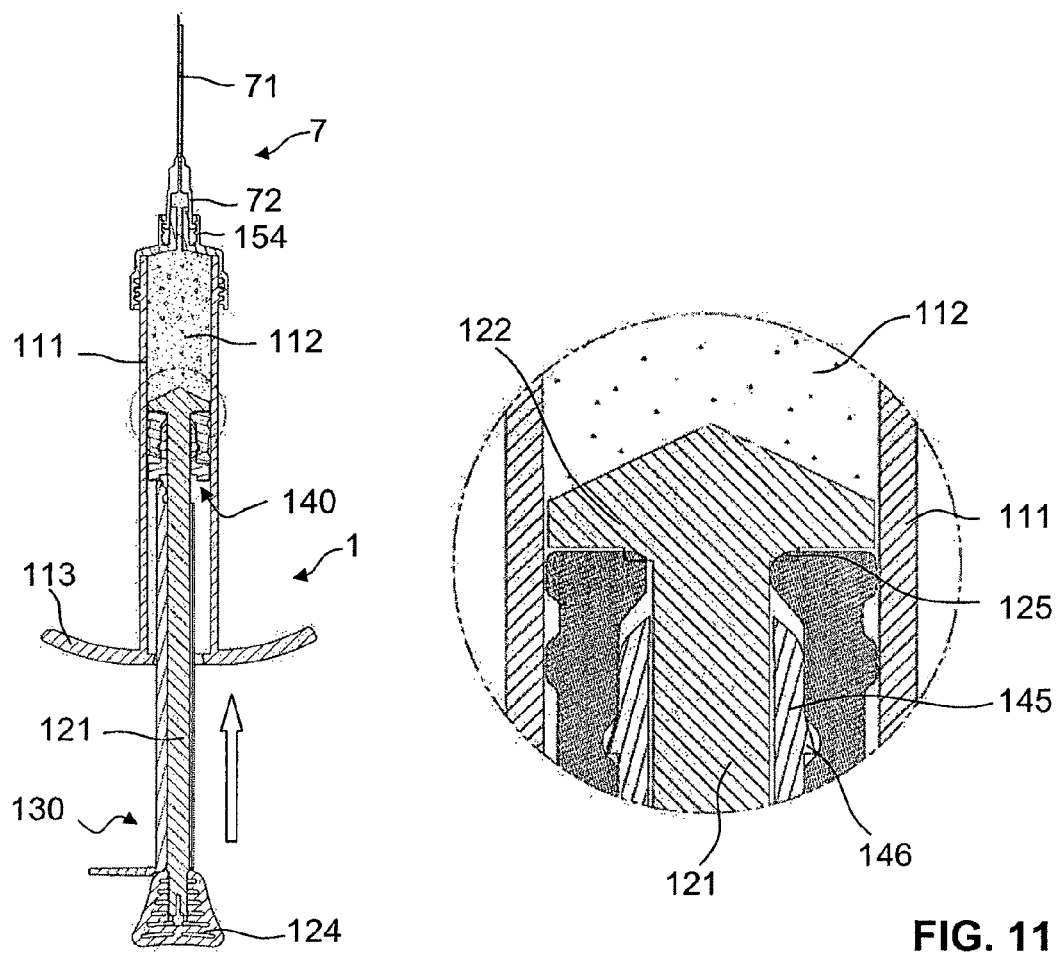
FIG. 10 a central section view of the discharging device of FIG. 1, with an injection attachment connected thereto, during discharging of the product.
FIG. 11 a partial section view of the region marked in FIG. 10.

In order to eject the product contained in the reservoir 112, which product is now mixed, the advancement element 120 is then withdrawn from the housing 110 up to the proximal end stop, and the securing element 130 is again clamped between the actuating handle 124 and the carrier sleeve 145. The piston 140 is then again coupled to the advancement element 120 and forms an airtight closing means of the reservoir 112 in the proximal direction. The end cap 6 is removed for ejecting the mixed product, and it is possible, for example, to place an injection attachment 7 onto the Luer connection 154, 155. To this effect the injection attachment 7 can comprise a female Luer cone 72. Furthermore, a hollow needle 71 can be provided on the injection attachment 7, which hollow needle 71 is used for injecting the product contained in the discharging device 1 into a patient. Injection takes place by advancing the advancement element 120 into the housing 1, as shown in FIGS. 10 (see direction of arrow) and 11.

As a matter of course the invention is not limited to the present exemplary embodiment, and a multitude of modifications are possible. For example it is not mandatory to provide a securing element 130. The advancement element could, for example, also comprise detent lugs that point radially outwards which in a manner similar to that of a bayonet coupling can be snapped into complementary indentations of the carrier sleeve by means of a combined longitudinal and rotary movement in order to couple the piston to the advancement element. To this effect the carrier sleeve could be non-rotationally guided in the housing.

The discharging device could, for example as is the case in document US 7,736,049, comprise a second reservoir that extends parallel to the first reservoir. The liquid could then be stored in this second reservoir. By sliding a second piston into this second reservoir, the liquid could be transferred, by way of a transfer region, to the first reservoir, where it would be mixed with a component contained therein and subsequently ejected. The first piston provided in the first reservoir would then be able to be coupled to and uncoupled from a correspondingly designed advancement element to which a mixing element is affixed.

Nor is it mandatory for the advancement element to extend through the piston. Also imaginable is a design of the discharging device in which the piston rod of the advancement element is designed as a tube that comprises a distal opening with a mixing element. Radially towards the outside this tube could, for example, be sealed off from the sidewall of the housing by means of O-rings. The piston would then be situated in the interior of this tube and would, for example, be affixed to an actuating rod that can be coupled to the tube. Radial indentations could then be provided on the radial outside of the piston, but this is not mandatory.

Instead of radial indentations on the inside or outside of the sealing element, it would also be possible to provide venting openings in the form of through-holes. The advancement element would then have to be correspondingly designed in such a manner that in the coupled state it closes off these holes or indentations.

However, the through-holes or radial indentations on the sealing element can in principle also be omitted. The sealing element could in the coupled state simply be pressed by its distal face against a circumferential end stop of the advancement element 120, which end stop points in the proximal direction, and could ensure the passage of air in the uncoupled state in that the internal diameter of the sealing element has a slightly larger diameter when compared to the external diameter of the piston rod.

A multitude of further modifications are possible.

The invention claimed is:

1. A discharging device for mixing and discharging a product, comprising:
    a housing that delimits a reservoir for the product, with a circumferential sidewall, an open proximal housing end and a distal housing end with an outlet opening;
    an advancement element that projects into the housing from the proximal housing end and that can be slid along a longitudinal direction relative to the housing, wherein the advancement element comprises a distal region with a mixing element for mixing the product; and
    a piston that is proximally arranged relative to the mixing element and that can be slid relative to the housing in the longitudinal direction in order to eject the product from the reservoir through the outlet opening,
    wherein the piston has an uncoupled state in which the advancement element can be slid relative to the piston in the longitudinal direction, and has a state in which it is coupled to the advancement element, in which state the piston can be slid in the longitudinal direction relative to the housing by means of the advancement element,
    wherein the piston in the coupled state together with the advancement element seals the reservoir in the proximal direction in an airtight manner towards the outside,
    wherein at least one of the piston and the advancement element in the uncoupled state frees at least one venting opening in proximal direction towards the outside,
    wherein the venting opening is arranged on the piston, and wherein in the coupled state the advancement element closes off the venting opening in an airtight manner,
    wherein the venting opening is designed as a radial indentation arranged on a radial inside of the piston,
    wherein the radial inside of the piston comprises a radially circumferential contact region in the region of the venting opening, which contact region widens in the distal direction radially towards the outside, and
    wherein the advancement element comprises a radially circumferential recess with an outside edge, which outside edge in the coupled state rests against the contact region so as to provide a circumferential seal.

2. The discharging device according to claim 1, wherein the advancement element extends through the piston.

3. The discharging device according to claim 1, wherein in the coupled state the venting opening is closed off by the mixing element.

4. The discharging device according to claim 1, wherein the piston and the advancement element seal the reservoir both in the coupled state and in the uncoupled state in such a manner that the reservoir in the proximal direction in terms of powdery and paste-like substances is impermeable towards the outside.

5. The discharging device according to claim 1, wherein the piston comprises a carrier sleeve and a sealing element, affixed to the carrier sleeve, which sealing element encloses the carrier sleeve.

6. The discharging device according to claim 5, wherein the venting opening is arranged on the sealing element.

7. The discharging device according to claim 1, wherein the piston is configured to be decoupled from the advancement element only when the piston has been withdrawn from the housing up to a proximal end stop.

8. The discharging device according to claim 1, further comprising a securing element that is configured to be attached to the advancement element so that the securing element is non-displaceable in the longitudinal direction relative to the advancement element, so that the piston is fixed in the longitudinal direction between the securing element and the mixing element, thus the piston being coupled to the advancement element through the securing element.

9. The discharging device according to claim 8, wherein in the coupled state the mixing element provides a distal end stop for the piston.

10. The discharging device according to claim 8, wherein in the coupled state the securing element in the proximal direction forms an end stop with an actuating handle that is affixed to the advancement element, and in the distal direction forms an end stop with the piston.

11. A discharging device for mixing and discharging a product, comprising:
    a housing that delimits a reservoir for the product, with a circumferential sidewall, an open proximal housing end and a distal housing end with an outlet opening;
    an advancement element that projects into the housing from the proximal housing end and that can be slid along a longitudinal direction relative to the housing, wherein the advancement element comprises a distal region with a mixing element for mixing the product; and
    a piston that is proximally arranged relative to the mixing element and that can be slid relative to the housing in the longitudinal direction in order to eject the product from the reservoir through the outlet opening,
    wherein the piston has an uncoupled state in which the advancement element can be slid relative to the piston in the longitudinal direction, and has a state in which it is coupled to the advancement element, in which state the piston can be slid in the longitudinal direction relative to the housing by means of the advancement element, wherein the piston in the coupled state together with the advancement element seals the reservoir in the proximal direction in an airtight manner towards the outside, wherein at least one of the piston and the advancement element in the uncoupled state frees at least one venting opening in proximal direction towards the outside, and wherein the piston comprises a carrier sleeve and a sealing element, affixed to the carrier sleeve, which sealing element encloses the carrier sleeve.

12. The discharging device according to claim 11, wherein the venting opening is arranged on the sealing element.

* * * * *